(12) United States Patent
Vojdani

(10) Patent No.: US 7,258,994 B2
(45) Date of Patent: *Aug. 21, 2007

(54) SALIVA IMMUNOASSAY FOR DETECTION OF ANTIBODIES FOR CARDIOVASCULAR DISEASE

(75) Inventor: Aristo Vojdani, Los Angeles, CA (US)

(73) Assignee: Immunosciences Lab., Inc., Beverly Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/328,963

(22) Filed: Jan. 9, 2006

(65) Prior Publication Data

US 2006/0094073 A1  May 4, 2006

Related U.S. Application Data

(62) Division of application No. 10/005,710, filed on Nov. 8, 2001, now abandoned.

(51) Int. Cl.
G01N 33/53 (2006.01)

(52) U.S. Cl. .................. 435/7.92; 435/7.1; 435/7.93; 435/7.94; 435/7.95; 436/513; 436/506; 436/507; 436/811

(58) Field of Classification Search .............. 435/7.1, 435/7.92–7.95, 960; 436/513, 506, 507, 436/811
See application file for complete search history.

(56) References Cited

U.S. PATENT DOCUMENTS

2003/0099929 A1    5/2003  Vojdani
2003/0100035 A1    5/2003  Vojdani

OTHER PUBLICATIONS

Oldstone, *J. Autoimmunity*, 2(Suppl.):187-194, 1989.
Srinivasappa et al., *J. Virology*, 57:397-401, 1986.
Talal et al., *J. Clin. Invest.*, 85:1886-1871, 1990.
Schoenfeld, Y., Serer, Y., Harats, D. "Atherosclerosis as an Infectious, Inflammatory and Autoimmune Disease." *Trends in Immunology*. 22:293-295 (2001).
Husband, A.M., Gowans, "The Origin and Antigen-Dependent Distribution of IgA-Containing Cells in the Intestine." *J Exp. Med* 1978; 148:1146-60.
Kagnoff, M.F., "Effects of Antogen-Feeding on Intestinal and Systemic Immune Responses. I. Primiing of Precursor Cytotoxic T Cells by Antigen Feeding." *J Immunol* 1978; 120: 395-399.
Mestecky, J., McGhee, J.R., Arnold, R.R., et al., "Selective Induction of an Immune Response in Human External Secretions by Ingestion of Bacterial Antigen." *J Clin Invest* 61: 731-737, 1978.
Cunningham-Rundles, C., Brandeis. W.E., et al., "Bovine Antigens and the Formation of Circulating Immune Complexes in Selective Immunoglobulin A Deficiency." *J Clin Invest.* 64:272-279, 1979.
Brandtzaeg, P., "Transport Models for Secretory IgA and Secretory IgM." Clin Exp. Immunol. 44:221-232, 1981.

Concha, E., Subiza, J.L., et al., "Disorders of Regulatory T Cells in Patients With Selective IgA Deficiency and its Relationship to Associated Autoimmune Phenomena." *Clin Exp. Immunol.* 49:410-418, 1982.
Bienenstock, J., Befus, A.D., "Some Thoughts on the Biologic Role of Immunoglobulin A." *Gastroenterology.* 84:178-185, 1983.
Romero-Piffiguer, Vucovich, P.R., and Riera, C.M., "Secretory IgA and Secretory Component in Women Affected by Reacidivant Vaginal Candidiasis." *Mycopathologia* 91:165-170, 1985.
Stone, A.A., Cox, D.S., et al., "Secretory IgA as a Measure of Immunocompetence.", *J. Human Stress.* 13:136-140, 1987.
Epstein, M.M., Baumgarten, A., "The Usefulness of Routine Screening For Salivary Secretory Component." *J Allerg Clin Immunol.* 88:356-360, 1991.
Rose, N.R., Herkowitz, A., et al. "Autoimmune Myocarditis: A Paradigm of Post-Infection Autoimmune Disease." *Immunology Today* 9: 117-120 (1988).
Kroes, I., Lepp, P.W., et al., "Bacterial Diversity Within the Human Subgingival Crevice." *Proc Natl Acad Sci USA.* 96, 14547-14552 (1999).
Bachmaier, K., Neu, N., et al., "*Chlamydia* Infections and Heart Disease Linked Through Antigenic Mimicry." *Science.* 283, 1335-1339 (1999).
Ridker, P.M., Kundsin, R.B., et al., "Prospective Study of *Chlamydia Pneumoniae* IgG Seropositivity and Risks of Future Myocardial Infarction." *Circulation.* 99, 1161-1164 (1999).
Rose, N.R., "Viral Damage of 'Molecular Mimicry'—Placing the Blaime in Myocarditis." *Nature Medicine* 6: 631-632 (2000).
Bachmaier, J., Le, J., et al., "'Catching Heart Disease': Antigenic Mimicry and Bacterial Infections." *Nature Medicine* 6: 841-842 (2000).
Parums, D.V., Brown, D.L., et al., "Serum Antibodies to Oxidized Low-Density Lipoprotein and Ceroid in Chronic Periaortitis." *Arch Pathol Lab Med* 114:383-387.
Salonen, J.T., et al., Autoantibody Against Oxidised LDL and Progression of Carotid Atherosclerosis. *Lancet* 339:883-887 (1992).
Schoenfeld, Y., et al., "Atherosclerosis as an Infectious, Inflammatory and Autoimmune Disease." *Trends in Immunology* 22: 293-295 (2001).
Wick, G., Schett, G., et al., "Is Atherosclerosis an Immunologically Mediated Disease?", *Immunology Today* 16, 27-33 (1995).
Shoenfeld, Y., et al., "Autoantibodies Associated with Atherosclerosis." *Ann Med.* 32 (Suppl. 1), 37-40 (2000).

(Continued)

*Primary Examiner*—Bao-Thuy L. Nguyen
(74) *Attorney, Agent, or Firm*—Knobbe, Martens, Olson and Bear, LLP

(57) ABSTRACT

A method for diagnosing the likelihood and severity of cardiovascular disease in a patient is disclosed. The method determines the levels of antibodies against autoantigens, including myosin, oxidized LDL, β-2-glycoprotein, heat shock protein-60, platelet glycoprotein, and immune complexes. It then compares the results to normal levels to determine the likelihood and severity of cardiovascular disease.

4 Claims, 6 Drawing Sheets

OTHER PUBLICATIONS

Shoenfeld, Y, et al., "Atherosclerosis and Autoimmunity." *Elsevier Science* (2001) 5-13.

McNeil, H.P., et al., "Anti-Phospholipid Antibodies Are Directed Against a Complex Antigen that Includes a Lipid-Binding Inhibitor of Coagulation: $\beta_2$-Glycoprotein I (Apolipoprotein H)." *Proc Natl Acad Sci USA* 87:4120-4124 (1990).

Galli, M., et al., "Anticardiolipin Antibodies (ACA) Directed Not to Cardiolipin But to a Plasma Protein Cofactor." *Lancet* 335:1544-1547 (1990).

Kandiah, D.A., Krilis, S.A., "Immunology and Methods of Detection of Antiphospholipid Antibodies." In *The Antiphospholipid Syndrome*. R.A. Asherson, R. Cervera, J.C. Piette and Y. Shoenfeld, eds., CRC Press. Boca Raton, FL p. 29-48 (1996).

Arvieux, J., et al., "Measurement of Anti-Phospholipid Antibodies by ELISA Using $\beta_2$-Glycoprotein I as an Antigen." *J. Immunol Methods* 143:223-229 (1991).

George, J., et al., "Adoptive Transfer of $\beta_2$-Glycoprotein I—Reactive Lymphocytes Enhances Early Atherosclerosis in LDL Receptor—Deficient Mice." *Circulation* 102, 1822-1827 (2000).

Sheng, Y., et al., "Anti- $\beta_2$-Glycoprotein I Autoantibodies From Patients With the 'Antiphospholipid' Syndrome Bind to $\beta_2$-Glycoprotein I Induces a Significant Increase in Anti-$\beta_2$-Glycoprotein I Antibody Affinity." *J. of Immunology* 161: 2038-2043 (1998).

Hegde, U.M., "Platelet Antibodies in Immune Thrombocytopenia." *Blood Rev* 6:34-42 (1992).

Hasselaar, P., et al., "Crossreactivity of Antibodies Directed Against Cardiolipin, DNA, Endothelial Cells and Blood Platelets." *Thromb Haemo* 63: 169-173 (1990).

Karpatkin, S., "Immunologic Thrombocytopenic Purpura in HIV-Seropositive Homosexuals, Narcotic Addicts and Hemophiliacs." *Semin Hemat* vol. 25, No. 3 (Jul. 1988) 219-229.

Ratner, L., "Human Immunodeficiency Virus-Associated Autoimmune Thrombocytopenic Purpura: A Review." *Am J Med* 86: 194-198 (1989).

McWilliams, N.B. Maurer, H.M., "Acute Idiopathic Thrombocytopenic Purpura in Children." *Am J Hematol* 7:87-96 (1979).

Cordiano, I., et al., "Biotin-Avidin Immobilization of Platelet Glycoproteins (BAIPG): A New Capture Assay For the Detection of Anti-Platelet Antibodies." *J Immunol Methods* 178 (1995) 121-130.

Theofilopoulos, A.N., et al., "The Raji Cell Radioimmune Assay For Detecting Immune Complexes in Human Sera." *J Clin Invest* vol. 57 (Jan. 1976) 169-182.

Aziz, M., et al., "Evaluation of Cell-Mediated Immunity and Circulating Immune Complexes as Prognostic Indicators in Cancer Patients." *Cancer Detection and Prevention*, 22(2): 87-99 (1998).

Strongin, Wendy. Laboratory Diagnosis of Viral Infections, Lennette, E. ed., Marcel Dekker, Inc., New York, pp. 211-219. 1993.

Kovanen, P., et al., "Prediction of Myocardial Infarction in Dyslipidemic Men by Elevated Levels of Immunoglobulin Classes A, E, and G, but Not M," *Arch Intern Med*, vol. 158, Jul. 13, 1998, pp. 1434-1439.

M. Puurunen, et al., "Antibody Against Oxidized Low-Density Lipoprotein Predicting Myocardial Infarction," *Arch Intern Med*, vol. 154, Nov. 28, 1994, pp. 2605-2609.

Co-Pending Related U.S. Appl. No. 10/004,929, filed Nov. 8, 2001,by Aristo Vojdani, entitled "Immunoassay in Blood and Saliva for Detection of Cardiovascular and Autoimmune Diseases: Differentiation Between Protective and Pathogenic Antibodies", currently being examined by Examiner David A. Venci in Group Art Unit No. 1641.

D. Externest, et al., "Correlations Between Antibody Immune Responses at Different Mucosal Effector Sites Are Controlled by Antigen Type and Dosage," *Infection and Immunity*, Jul. 2000, vol. 68, No. 7, pp. 3830-3839.

Mean ± SD of IgA antibody levels in 30 saliva samples from controls ☐, patients with cardiovascular disease ▨, and autoimmune disease ▬.

FIG. 6

CORRELATION BETWEEN REACTIVITY OF ANTIBODY TO AUTOANTIGEN AND MEDICAL CONDITION

Reactivity of Saliva IgA Antibody Against:

| Myosin Antibody | Oxidized LDL | Heat-Shock Protein-60 Antibody | B-2 Glycoprotein-1 Antibody | Immune Complex | Medical Condition |
|---|---|---|---|---|---|
| - | - | - | - | - | Optimal |
| + | + | + | + | + | Possible Atherosclerosis |

```
SEQUENCE LISTING

<160> NUMBER OF SEQ ID NOS: 2

<210> SEQ ID NO 1
<211> LENGTH: 15
<212> TYPE: PRT
<213> ORGANISM: mouse M7A-alpha peptide MA'ST motif

<400> SEQUENCE: 1

Ser Leu Lys Leu Met Ala Thr Leu Phe Ser Thr Tyr Ala Ser Ala
1               5                   10                  15

<210> SEQ ID NO 2
<211> LENGTH: 19
<212> TYPE: PRT
<213> ORGANISM: Human HSP60 peptide

<400> SEQUENCE: 2

Ala Met Thr Ile Ala Lys Asn Ala Gly Glu Gly Ser Leu Ile Val Glu
1               5                   10                  15

Lys Ile Met
```

SALIVA IMMUNOASSAY FOR DETECTION OF ANTIBODIES FOR CARDIOVASCULAR DISEASE

RELATED APPLICATION DATA

This application is a divisional application of U.S. patent application Ser. No. 10/005,710 filed Nov. 8, 2001 now abandoned, the entirety of which is hereby incorporated by reference.

BACKGROUND OF THE INVENTION

1. Field of the Invention

The invention relates to a saliva immunoassay for detection of antibodies for cardiovascular disease.

2. Description of the Related Art

Cardiovascular disease is predicted to be the most common cause of death worldwide by the year 2020. Half of heart disease patients lack established risk factors such as elevated lipids, hypertension, tobacco abuse, and positive family history. Additionally, these risk factors are generally associated with the disease, and the exact mechanism by which they may contribute to the development of atherosclerosis is not clear. However, previous and recent studies point to a linkage between infection with different bacteria and heart disease in the other 50% of observed incidences. Pathogenesis of the disease induced by infectious agents is described by three different mechanisms of action: release of toxins or superantigens, induction of inflammation, and molecular mimicry or cross-reactivity. This may result in plaque formation or antimyosin cellular and humoral immunity and subsequently, to myocarditis or other autoimmune diseases.

Through the years, many reports have incriminated various infectious agents in the pathogenesis of autoimmune disease. Moreover, the American College of Cardiology has issued a list of harmful pathogens as possible links to heart disease.

Traditionally, it is assumed that infectious agents induce disease by direct tissue damage via secretion of toxins or different antigens, particularly myosin. These toxins may directly or indirectly induce tissue damage and cause release of tissue antigens.

An infectious agent can be taken up by macrophages and transferred to the bloodstream and arteries. When a macrophage burrows into the wall of a blood vessel to take in irritants such as LDL and oxidized LDL, it transfers the infectious agent into the neighboring arterial cells. Infected arterial cells then attract more macrophages and other inflammatory responses, such as platelets, and then die. If this vicious cycle of inflammation continues, it can result in fibrous lesions or plaque formation. When pieces of the plaque break loose, they can start blood clots and cause heart attack.

Another mechanism by which infectious agents can cause autoimmune disease is molecular mimicry. Molecular mimicry is defined as structural similarity between antigens coded by different genes. Antigenic cross-reactivity between host and bacteria is exemplified by blood group substances and bacterial polysaccharides; cardiac tissue and streptococcal proteins; and kidney tissue and E. coli polysaccharides. Viruses may also induce autoimmune responses through shared determinants on molecules notably present on host cells, by altering the host immune system, or by causing the expression or release of "normally sequestered" self antigens.

Harmful pathogens may be the cause of many human diseases. These pathogens may induce their pathologic response through one of the above-mentioned mechanisms of action.

Many viruses, bacteria, and even parasites are claimed to affect atherosclerosis plaque deposition. Among them, Chlamydia pneumoniae probably has the strongest association with atherosclerosis. There is a close relationship between C. pneumoniae infection, IgG and IgM titers, and increased evidence of MI, CVA, and peripheral vascular disease (PVD). C. pneumoniae antigens are found in atherosclerosis plaques, and T-cell reactions to these antigens have been demonstrated. Experimental models illustrate the pathogenic role of C. pneumoniae and the unique heat shock protein (HSP)-60. Other major atherosclerosis-associated pathogens are Helicobacter pylori, Epstein-Barr virus and cytomegalovirus. For some pathogens, interfering pathogenic mechanisms have been described, such as cytomegalovirus gene-induced proliferation of smooth-muscle cells. From data showing a correlation between increased atherosclerosis incidence and chronic bronchitis, as well as periodontitis, it has been suggested that any infectious agent, and especially multiple chronic infections, could result in accelerated atherosclerosis formation. This multiplicity was confirmed recently in experimental animal models. There is no doubt therefore, that chronic infections with specific or nonspecific infectious agents can contribute to the acceleration of atherosclerosis development, either by nonspecific mechanisms [hypercoagulation and increased adhesion molecule and elevated C-reactive protein (CRP) levels] or by more specific mechanisms, such as induction of HSP-60 expression and eventually pathogenic anti-HSP-60 antibody production.

Autoantibodies are frequently found in the sera of virus-infected individuals, both during and after infection. For example, after infection with Epstein-Barr virus (EBV), antibodies reacting with intermediate filaments of cells, immunoglobulin or thyroglobulin were detected (Oldstone, J. Autoimmunity, 2(Suppl.):187-194, 1989; Srinivasappa et al., J. Virology, 57:397-401, 1986; Talal et al., J Clin. Invest., 85:1886-1871).

Myosin Antibody

Myosin accounts for over 50% of muscle proteins. Along with actin, myosin is involved in muscle contraction. Myosin is one of the largest proteins in the body, with a molecular mass of 500 kDa. Due to its large mass, antigenic mimicry between infectious agents and myosin molecules is highly probable.

It is now well-known fact that infectious agents are associated with human myocarditis. The development of autoimmunity to myocardial antigens has been widely recognized after myocardial infarction or after cardiac surgery. Autoantibodies to heart tissue in patients with rheumatic carditis, post-myocardial infarction and post-pericardiotomy syndromes have been described. Antibodies against heart tissue can also occur in patients with post-infection myocariditis, dilated cardiomyopathy, rheumatic carditis, Chagas disease, and adriamycin cardiotoxicity. It has also been observed that serum from patients with myocarditis reacted specifically with sarcolemmal and cytoplasmic heart antigens. Moreover, serum samples containing circulating heart antibodies also induced complement-mediated myocyte lysis and antibody-dependent cell-mediated cytotoxic reactions in vitro, suggesting that they may be pathogenic in myocarditis.

It is now clear that some patients with active myocarditis or cardiomyopathy carry antibodies to the mitochondrial adenine nucleotide translocator. Such patients, whose serum inhibit in vitro ADP-ATP translocator activity, have reduced cardiac function relative to their counterparts without these antibodies. The existence of multiple heart-reactive antibodies in autoimmune heart disease is consistent with the presence of multiple tissue- and organelle-specific antibodies in both systemic lupus and autoimmune thyroiditis.

For years it has been known that Chlamydia can induce cardiovascular disease in experimental animals. This Chlamydia-mediated heart disease in mice can be induced by antigenic mimicry of a heart muscle-specific protein, thus providing a molecular link between Chlamydia infections and heart disease. Since many infectious agents have been implicated in heart disease, it is not surprising that organisms other than Chlamydia can also supply mimicking epitopes. Indeed, Machmaier, K. et al., in a study published in Nature Medicine in August 2000, screened public databases for proteins sharing the pathogenic mouse M7Aα peptide MA'ST motif (whose amino acid sequence is as follows: SLKLMATLFSTYASA). This motif is found in proteins from a multitude of viruses, bacteria, fungi, and protozoa, which are involved in cardiovascular disease.

Cross-reactive antibodies appear to be quite common in patients with rheumatic fever. Some of these autoantibodies could be absorbed by certain streptococcal strains, and some reacted specifically with cardiolipin and tropomyosin. Group A and mutant streptococci share a common epitope with cardiac myosin, which may be associated with the heavy meromyosin region of the molecule. In Chagas disease—caused by the protozoan parasite *Trypanosoma cruzi*—heart autoantibodies react with laminin, while Chagasic cardiomyophathy may be due to recognition of the calcium-sequestering ATPase in the sarcoplasmic reticulum.

Oxidized LDL Antibody

Oxidized Low Density Lipoprotein (oLDL), the prime candidate for an autoantigen, plays a critical role in the development and progression of atherosclerosis and other vascular diseases. It is incriminated in foam cell generation through uptake by the unregulated scavenger receptors on macrophages.

Recent evidence suggest that autoantibodies against oxidatively modified LDL can be used as a parameter that consistently mirrors the occurrence of oxidation processes taking place in vivo. In fact, elevated levels of autoantibodies against oLDL have been detected in the bloodstream of patients with coronary artery disease. Moreover, recent studies indicate a correlation between autoantibodies against oLDL and the progression of carotid atherosclerosis. Increased serum concentrations of oLDL have also been described in various diseases such as pre-eclampsia and systemic lupus erythematosus (SLE).

Heat Shock Protein 60 (HSP60) Antibody

Heat Shock Protein 60 (HSP60), also known as CPN60, is an abundant protein synthesized constitutively in the cell that is induced to a higher concentration after brief cell stress or shock. It is present in all species analyzed so far and exhibits a remarkable sequence homology among various counterparts in bacteria, plants, and mammals: more than half of the residues are identical between bacterial and mammalian HSP60. The ubiquitous occurrence and remarkable evolutionary conservation suggests that HSP60 may play an essential role in the cell. It is now believed that HSP60, which is localized in mitochondrial matrix in eukaryotes, interacts with multiple proteins during translocation and/or folding. *E. coli* HSP60 (GroEL) has been shown to catalyze folding of many proteins in vitro and is involved in the assembly of bacteriophage lambda proteins during infections. TCP-I, a member of the HSP60 family, has similar functions to HSP60 but is localized within the cytoplasm. Bacterial HSP60 proteins are major targets of immune responses during infection, and the highly conserved nature of bacterial and mammalian HSP60 has led to speculation that immune reactivity to these stress proteins may be a component of certain autoimmune diseases and atherosclerosis. In fact, G. Wick (Innsbruck, Austria) first claimed that HSP60 is involved in atherosclerosis. Anti-HSP60 antibody titers correlate with the degree of atherosclerosis in carotid ultrasound studies. The increase in anti-HSP60 antibody levels could result from direct turbulence damage to bifurcated arteries or could be caused by infectious agents (e.g. *C. pneumoniae*) releasing HSP60, which becomes immunogenic. T-cell lines cultured from the atherosclerosis plaque proliferate when exposed to HSP60 and both the autoantibodies, as well as the autoantigen can be found in the plaque. Finally, active immunization of rabbits and apolipoprotein-E or low-density lipoprotein (LDL)-receptor knockout mice with HSP60 leads to accelerated formation of atherosclerosis plaques.

Anti-β2-Glycoprotein-1

β2-Glycoprotein-1 (p2GP1) is a normal glycoprotein synthesized by the liver that behaves as an anti-coagulant and is also an anti-atherogenic agent. This glycoprotein, also known as apolipoprotein-H, is a human plasma glycoprotein that consists of a single polypeptide of 326 amino acids with a molecular weight of 50 kDa.

It is now widely accepted that β2GP1 is an absolute requirement for the binding of "antiphospholipid" (aPL) Abs purified from patients with autoimmune disease when assayed using anionic phospholipid ELISAs. These autoantibodies are of considerable clinical importance because of their association with arterial and venous thrombosis, recurrent fetal loss, and thrombocytopenia. The interaction of autoantibodies with β2GP1 may be important in relation to the pathogenesis of thrombosis in vivo. β2GP1 is known to bind to negatively charged surfaces as well as to activated platelets and to act as an inhibitor of the intrinsic blood coagulation pathway in vitro.

β2GP1 also binds to oLDL. This binding of β2GP1 to oLDL reduces the uptake of oLDL by scavenger receptors on macrophages. In fact, β2GP1 is found in the atherosclerosis plaque and is the target antigen in antiphospholipid syndrome (APS). Antibody titer to β2GP1 correlates with atherosclerosis. In in vitro conditions, these antibodies enhance uptake of oLDL by macrophages.

Recently, in a classical study, accelerated atherosclerosis plaque formation was induced in LDL-receptor-deficient mice by the passive transfer of lymphocytes from the lymph nodes and spleens of mice actively immunized with β2GP1.

Anti-Platelet Glycoproteins

A number of diseases and syndromes are thought to involve antibody, or immune complex-mediated platelet destruction. Among these are both the acute and chronic forms of idiopathic thrombocytopenic purpurea; the closely related thrombocytopenia of systemic lupus erythematosus; quinidine, apronalide, and other drug-induced thrombocytopenias; post-transfusion purpurea; neonatal isoimmune thrombocytopenia; and the alloimmunization that renders multi-transfused patients refractory to random platelet transfusion.

Platelet function and number can both be affected in immune-mediated diseases; however, thrombocytopenia is by far the more common finding. Abnormalities of platelet number and function can occur via any of several immune mechanisms. Both humoral and cell-mediated immune mechanisms can produce thrombocytopenia. The most commonly considered, although by no means the most commonly noted, immune mechanism for thrombocytopenia is the formation of specific antiplatelet autoantibodies. Platelets have a large number of immunogenic structures on their surface, with the glycoprotein IIb/IIIa (GP IIb/IIIa) complex being the most numerous. It is not surprising, therefore, that autoantibodies directed against epitopes on the GP IIb/IIIa complex are the most frequent when the specificity of the autoantibodies have been determined in blood. Platelet autoantibodies are usually of the IgG immunoglobulin class, although IgA, IgD, and IgM autoantibodies have been demonstrated occasionally. Complement has also been found on surface of platelets in clinical syndromes consistent with increased immune-mediated platelet destruction. However, most autoantibodies are not complement fixing, and removal of the immunoglobulin-coated platelets occurs in the spleen and other sites of reticuloendothelial tissue.

Immune Complexes

Immune complexes are formed when antigens bind with antibodies. Antigen-antibody complexes can activate the complement cascade and bind the C1q component of complement and form pathologic complexes.

Both exogenous and endogenous antigens can trigger pathogenic immune responses that result in immune complex (IC) disease. Because circulating IC's play such an important part in many diseases, including autoimmunity, neoplasms, infectious diseases due to bacteria, viruses, and parasites, and other unclassified disorders, the demonstration of IC's in tissues and biological fluids has achieved rising prominence.

There are a number of cases in which immune complexes assays are helpful in the diagnosis and monitoring of disease activity, for example, lupus and arthritis.

The fact that SLE is considered the prototype of human immune complex disease has led to studies of SLE with almost every type of immune complex assay developed. A high incidence of positive tests and disease activity has been uniformly reported. There is considerable evidence that DNA-anti-DNA complexes are involved in the pathogenesis of SLE. Immune complex determinations coupled with detection of serum antibodies to native DNA and determinations of levels of hemolytic complement (CH50) in serum are useful diagnostic tests. Most studies have found a correlation between positive immune complex assays and antibodies to native DNA, which is the most important laboratory marker of lupus. Several serial studies have indicated that the C1q solid-phase assay correlates better with disease activity than do other immune complex tests.

The role of circulating immune complexes (CIC) in cancer is of particular interest because tumors express antigens that elicit both cellular and humoral immune responses. CMI in tumor-bearing host is blocked by CIC or "blocking factors" in circulation. Antigen-antibody complexes are formed by noncovalent hydrophobic coulombic hydrogen bonds. The nature and quantity of CIC detected in circulation is dependent upon the dynamics of formation, clearance, and tissue deposition of immune complexes. Immune complexes cause tissue injury through the terminal lytic component of activated complement system. Since activated complement components are strong chemotactic agents, leukocytoclastic vasculitis is seen in cancer patients with high levels of CIC.

Manifestation of Antibodies

The deposition of antigens in the gut has been shown to lead to the production of IgA antibodies in secretions at sites distant from the gut, such as colostrums, lacrimal and salivary secretions in man and salivary secretions in rhesus monkeys and in rats.

A general conclusion therefore is that the secretory immune system can be stimulated centrally and that precursors of IgA-producing cells migrate from the gut-associated lymphoid tissue to several secretory sites in addition to the lamina propria of the gut itself. Therefore, if antigens are injected into the submucosal tissues, they are likely to induce serum IgG antibodies as well as secretory IgA antibodies in saliva. However, if it is applied topically to the skin or to the intraepiethelial tissue, secretory IgA is the main product which is detected in saliva. The role of topically applied antigen in the localization and persistence of IgA responses has been demonstrated in several secretory sites, including the respiratory tract, oral cavity, gut, and vagina.

The evidence that cells migrate from the gut to various secretory tissues, and that immunization in the gut leads to antibodies at various secretory sites has led to the concept of a common mucosal system. However, this concept may be an oversimplification, since although immunization in the lung may lead to antibodies in distant secretory sites, such as salivary glands and immunization in the lacrimal glands has also been shown to lead to the production of antibodies in saliva. Thus, with firm evidence that antigen deposition in the gut may lead to antibodies not only in the gut but also in saliva, lungs, lacrimal secretions and genitourinary tract, it is probably more correct to designate the system as an enteromucosal system.

Saliva is a source of body fluid for detection of an immune response to bacterial, food, and other antigens present in the oral cavity and gastrointestinal tract. Indeed, salivary antibody induction has been widely used as a model system to study secretory responses to ingested material, primarily because saliva is an easy secretion to collect and analyze. It seems to be a general feature that salivary IgA antibodies can be induced in a variety of species in the absence of serum antibodies. This has been demonstrated after immunization with particulate bacterial antigens in human could selectively induce an immune response to *Streptococcus mutans* by oral administration of the antigen. This route of administration resulted only in antibody production in saliva and not in serum. Similar mucosal immune response in the form of saliva IgA did occur in monkeys, rabbits, rats, and mice after oral administration of *Streptococcus mutans* or other bacteria.

This lack of production of IgG, but IgA production in saliva after oral or intragastric administration of bacterial antigens is shown in the following table.

TABLE 1

Induction of salivary IgA antibody after stimulation of gut associated lymphoid tissue

| Species | Antigen | Route of Administration | Salivary IgA Production | Serum Antibody Production |
|---------|---------|------------------------|-------------------------|---------------------------|
| Human | *Streptococcus Mutans* | Oral | ++ | − |
| Monkeys | *Streptococcus Mutans* | Intragastric | ++ | − |
| Rabbits | *Penumococcus* or BGG | Intragastric | ++ | − |
| Rats | *Streptococcus Mutans* | Oral | ++ | − |
| Mice | *Streptococcus Mutans* or Ovalbumin | Intragastric | ++ | − |

As indicated in this table, oral or intragastric administration of dietary soluble proteins such as bovine gammaglobulin (BGG) and ovalbumin or eggalbumin resulted in salivary IgA production but not in any antibody production in serum. For these reasons, saliva has been selected not only because of its relevance in oral disease, but mainly because it is an accessible fluid, easy to collect, and is thought to show representative responses in secretions after central or intragastric immunization. However, if both saliva IgA and serum IgG antibodies are detected in the same patient, it means that this individual has been primed with the antigen orally as well as systematically.

This IgA production in saliva and IgG production in serum is dependent upon antigen dosage as well as the integrity of the gut. For example, a single intragastric immunization with 1 mg of eggalbumin led to oral tolerance but did not lead to detectable secretory IgA antibodies, whereas 10 mg of ovalbumin led to systemic tolerance, but to a significant level of salivary IgA antibodies. Thus, detection of high levels of antibody in saliva is an indication of the body's exposure to significant levels of antigenic stimulation.

While this concept of oral tolerance to high doses of soluble antigen may be correct, certain conditions—such as overloading of the GI tract with bacterial toxins—may not lead to oral tolerance. This is due to the fact that bacterial toxins will cause the opening of tight junctions, which will in turn lead to the absorption of ingested proteins and bacterial antigens from the gut in significant amounts. This excessive uptake of bacterial, fungal, viral, and dietary proteins into the circulation may induce immune response first in the form of IgM, and thereafter in the form of IgG and IgA antibodies in the serum, all of which may lead to different clinical conditions.

SUMMARY OF THE INVENTION

One aspect of the preferred embodiment is a method for diagnosing the likelihood and severity of cardiovascular disease in a patient. This method includes (a) determining a level of antibodies against an autoantigen or a corresponding recombinant antigen or synthetic peptide for cardiovascular disease in a sample from the patient and (b) comparing the level of antibodies determined in step (a) with normal levels of the same antibodies.

Possible outcomes for the comparison include (i) normal levels of autoantigen antibodies for cardiovascular disease indicate optimal conditions; and (ii) higher than normal levels of autoantigen antibodies for cardiovascular disease indicate ongoing pathology or prediction of early pathogenic reaction for cardiovascular disease.

In one embodiment, autoantigens are myosin, oLDL, HSP60, β2GP1, platelet glycoprotein, or immune complexes.

In one embodiment, an ELISA test is used to determine the levels of antibodies.

In one embodiment, the antibodies, preferably IgA antibodies, are measured from saliva.

Further objects, features and other advantages of the preferred embodiments become apparent from the ensuing detailed description, considered together with the appended figures.

BRIEF DESCRIPTION OF THE DRAWINGS

FIG. 6 is a table showing the correlation of reactivity of saliva IgA antibody against infectious agents and autoantigens to cardiovascular disease.

DETAILED DESCRIPTION OF THE PREFERRED EMBODIMENT

Figure 1:
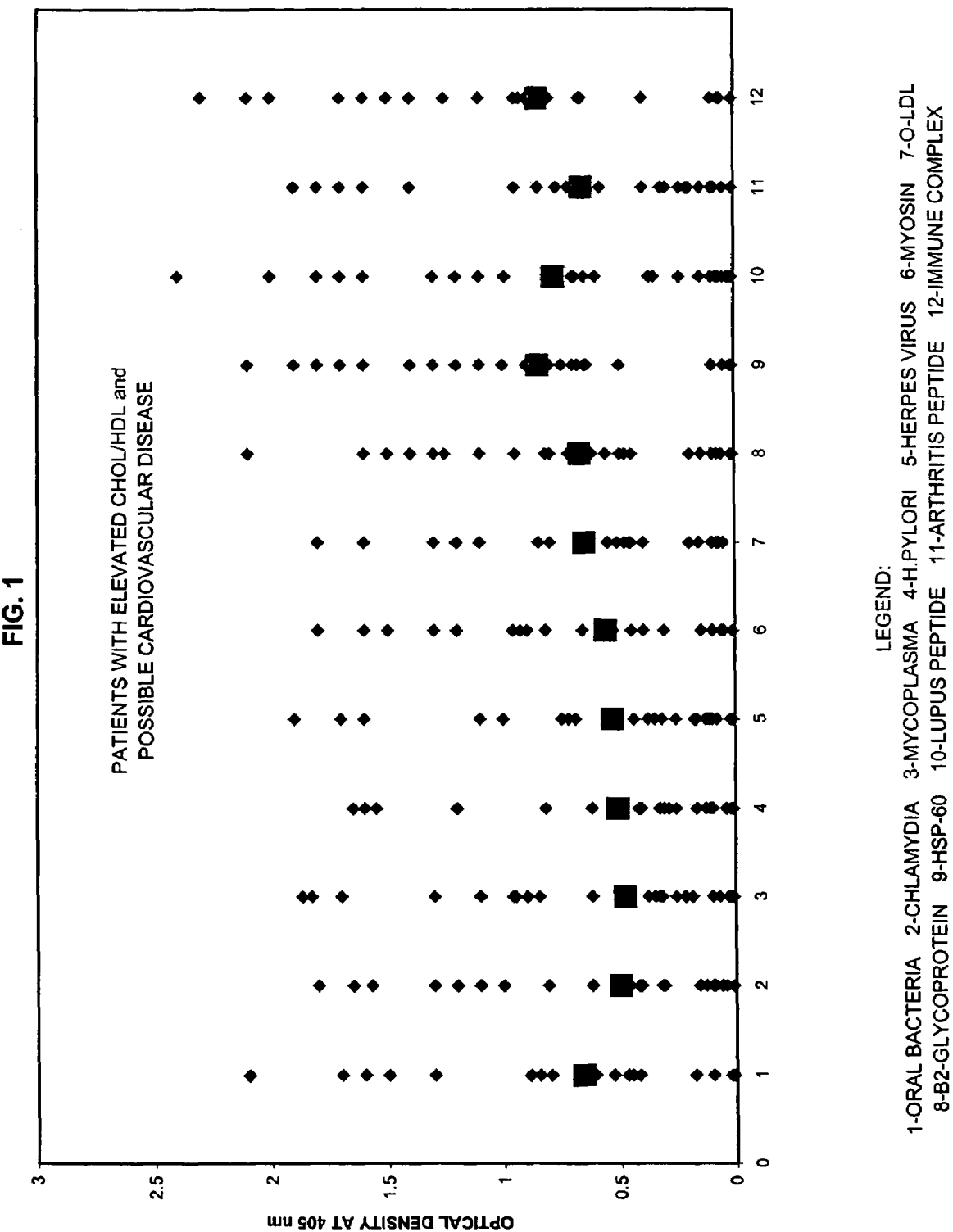
FIG. 1 is a graph showing saliva IgA antibodies against infectious agents, specific and non-specific autoantigens involved in cardiovascular disease and autoimmune disease expressed by O.D.'s from patients with possible cardiovascular disease.

The inventor has developed a single test that will accurately inform the physician of important clinical conditions required to diagnosing in patients the likelihood and severity of cardiovascular disease. The test utilizes a highly sensitive and accurate ELISA test method that measures saliva IgA specific antibody titers to the purified antigens or a corresponding recombinant antigen or synthetic peptide from autoantigens.

Such quantitative and comparative test results allow the physician to determine cardiovascular autoimmune disease. The test thus helps the clinical investigator to evaluate and treat patients by using immunological responses as indications of cardiovascular autoimmune disease.

The test involves determining the level of antibodies against an autoantigen or a corresponding recombinant antigen or synthetic peptide for cardiovascular disease. The level of antibodies against autoantigens for cardiovascular disease is compared between test samples of a patient and normal controls. A higher than normal level of antibodies against autoantigens for cardiovascular disease, such as myosin peptides, oLDL, HSP60, β2GP1, platelet glycoprotein, and immune complexes, indicate a presence or possibility of cardiovascular disease.

Defined autoantigens involved in atherosclerosis include the following: myosin, oxidized LDL (oLDL), Heat Shock Protein-60 (HSP60), β-2-Glycoprotein-1 (β2GP1), cardiolipin, platelet glycoproteins, and immune complexes.

Chronic infections and the resulting production of antibodies against them can accelerate atherosclerosis by means of specific and non-specific mechanisms. Myosin, HSP60, oLDL, and β2GP1 are defined autoantigens involved in specific mechanisms for the induction of cardiovascular disease. Platelet glycoproteins, immune complexes, endothelial cell antigens and intracellular adhesion molecules are indirect factors involved in non-specific mechanisms for the induction of cardiovascular disease.

The detection of specific biomarkers, such as myosin, oLDL, β2GP1, and HSP60 antibodies in saliva along with non-specific markers, such as platelet glycoprotein antibodies, elevated immune complexes, endothelial cell antibodies and intracellular adhesion molecules may detect ongoing pathology or predict early pathogenic reaction. Because of this, preventive measures may be taken to reverse the course of action of the disease. As compared to healthy controls, patients with elevated lipid profile profile (Cholesterol/HDL ratio of >7 and a blood pressure >140/80) have a much higher level of antibodies against the defined autoantigens (myosin, HSP60, oLDL, and β2GP1). There may also possibly be elevated levels of immune complexes, C-reactive proteins, and intracellular adhesion molecules.

Although other materials and methods similar or equivalent to those described herein can be used in the practice or testing of the preferred embodiments, the preferred method and materials are now described.

EXAMPLE 1

General Procedures for Immunity Panel for Cardiovascular Disease

For the test, about 2 ml of patient saliva was collected. Saliva specimen was kept at −20° C. until the performance of the assays.

The purified antigens were immobilized by attachment to a solid surface, such as a microtiter plate. The saliva sample was added to the plate followed by incubation and washing. Antibody bound to antigen was revealed by adding enzyme labeled monoclonal antibody directed against the first immunoglobulin. After addition of substrate, color development was measured by microtiter reader at 405 nm. The intensity of the color was directly related to the concentration of antibodies to these antigens present in patient's specimen.

Saliva samples were collected in the morning, before brushing teeth, smoking, or drinking. 2 ml of saliva was collected. Saliva was collected after a gentle chewing action in a test tube containing 0.1 ml of preservative. Saliva specimen was kept at −20° C. until the performance of the assays.

Calibrator samples I, II, III as well as positive and negative controls were used.

The wash buffer was made as follows: in a 500 ml graduated cylinder, 450 ml of water was added to 50 ml of 10× wash buffer. It was mixed and transferred to a 500 ml squeeze bottle and stored at 2-8° C. until used.

Substrate buffer and Stop Solution were ready for use. (CAUTION: Both solutions are caustic: avoid contact with skin and eyes, rinse with copious amounts of water in event of contact.)

The substrate solution was prepared only immediately before use. For 1-5 strips, 5 ml of substrate buffer were pipeted into the empty substrate reconstitution bottle and 1 substrate tablet was dropped in. The bottle was shaken to dissolve the tablet. The buffer was used within an hour after reconstitution as recommended.

Reagent and specimen were prepared as follows. All strips to be used, reagents, controls, and patient's specimen were equilibrated to room temperature (22-25° C.). Patient's specimen was diluted 1:100 with specimen diluent buffer: 20 μl specimen+2.0 ml buffer. Specimen dilutions were made in tubes prior to addition to wells and thoroughly mixed before dispensing. Only one well per test was necessary. For every determination, six strips (1-6) of eight wells were needed to run blank calibrators and four patient's samples.

Well Identification: 6 antigen-coated strips were used. Each was divided into 8 equal-sized squares. The top 6 squares were labeled "BLANK", the next 3 were "CALIBRATOR I, CALIBRATOR II, and CALIBRATOR III". The last 4 were labeled "SPECIMEN I, SPECIMEN II, SPECIMEN III and SPECIMEN IV". Note: Blank and calibrators may need to be positioned differently if specified by the instrument manufacturer. For each test performance the following wells were used: One blank well (reagent blank), one well each for Calibrator I, II and III, and one well each for patient specimens.

The assay procedure was as follows: 100 μl of specimen diluent buffer was pipeted into all eight wells of strip # 1, 2, 3, 4, 5, and 6. The contents were discarded and the addition of specimen diluent buffer to the same wells was repeated. Then, 100 μl of each calibrator or patient specimen dilutions were pipetted into identified wells; being careful to avoid splashing and air bubbles because cross-contamination between the wells may cause erroneous results. Then, 100 μl of specimen diluent buffer was pipeted into a blank well. The reagents were dispensed slowly to avoid splashing and air bubbles. If large air bubbles occurred, they were aspirated or the plate was gently shaken. The plate was covered and incubated for 60 minutes at room temperature (22-25° C.). Specimen was shaken from the wells into a container containing disinfectant solution or aspirated with a vacuum device. All wells were empty prior to filling with 1× wash buffer and allowing a 10-20 second soak time. The wells were emptied by shaking into a disposal container or aspirated. Washing was repeated three more times. The inverted plate was tapped onto a paper towel to completely remove all residual liquid. Then, 100 μl of anti IgA conjugate was added to the tested strips. The plate was covered and incubated for 60 minutes at room temperature (22-25° C.). The liquid was shaken or aspirated from all the wells and washed four times. Then, 100 μl of p-NPP substrate was added to all the wells at timed intervals that corresponded to the reading time of the instrument used to read the reactions. The 45-minute incubation time was started as substrate was added to the first well. The plate was covered and incubated 45 minutes at 22-25° C. (The assay may be incubated for less than 45 minutes if incubation temperature is higher than 25° C.). Then, 50 μl of 3N NaOH was pipeted into all the wells at the same timed intervals that the p-NPP was added. The plate was shaken for 1-2 minutes by hand or on a shaker, avoiding splashing. The bottom of the wells was wiped with a non-abrasive paper towel and the instrument was zeroed on the blank well. The OD was read at 405±5 nm within 30 minutes, and reactions recorded.

The ELISA values for the calibrators used in this test system were according to the samples used in the test.

ELISA values for each test specimen were determined using the following formula:

$$ELISA \text{ values of test specimen} = \frac{\text{Values of calibrator} \times \text{Absorbance of test specimen}}{\text{Aborbance of calibrator}}$$

EXAMPLE 2

Test for Myosin Antibody

Myosin pathogenic peptide "SLKLMATLFSTYASA" was synthesized by a robotic multiple peptide synthesizer and resin was used as solid support. Peptide was characterized by reversed-phase HPLC and electrospray mass-spectrometry with purity greater than 80%. This peptide was bound to bovine serum albumin and used for coating microtiter plates.

Each well of microtiter plate was coated with 3 μg peptide in 0.1 M carbonate buffer pH 9.5. After 24 hours incubation and washing, 200 ml of 2% BSA was added and incubated for an additional 2 hours. Plates were washed, dried, and used for measurement of myosin antibodies. The test specimen was added to the plate followed by incubation and washing. The procedure in Example 1 was followed to measure for the myosin antibodies.

The ELISA values for the calibrators used in this test system were as follows: Calibrator I=7.5, Calibrator II=15, and Calibrator III=30.

The ELISA values for each test specimen were determined using the formula in Example 1.

EXAMPLE 3

Test for Oxidized LDL Antibody

Wells of microtiter polystryrene plate were coated with 3 μg of oLDL in 100 μl of 0.1 M carbonate buffer pH 9.6 and were kept overnight at 4° C. The plates were then washed with PBS and blocked with 2% BSA for 2 hours at room temperature. Plates were washed, dried, and used for detection of antibodies against oLDL. The test specimen was added to the plate followed by incubation and washing. The procedure in Example 1 was followed to measure for oLDL antibodies.

The ELISA values for the calibrators used in this test system were as follows: Calibrator I=37, Calibrator II=75, Calibrator III=300, and Calibrator IV=1200.

The ELISA values for each test specimen were determined using the formula in Example 1.

EXAMPLE 4

Test for Heat Shock Protein 60 Antibody

Human HSP60 Peptide "AMTIAKNAGEGSLIVEKIM" was synthesized by a robotic multiple peptide synthesizer and resin was used as solid support. Peptide was characterized by reversed-phase HPLC and electrospray mass-spectrometry with purity greater than 80%. This peptide was bound to bovine serum albumin and used for coating microtiter plates.

Each well of microtiter plate was coated with 3 μg of peptide in 0.1 M carbonate buffer pH 9.5. After 24 hours of incubation and washing, 200 μl of 2% BSA was added and incubated for an additional 2 hours. Plates were washed, dried, and used for measurement of HSP60 antibodies. The test specimen was added to the plate followed by incubation and washing. The procedure in Example 1 was followed to measure for HSP60 antibodies.

The ELISA values for the calibrators used in this test system were as follows: Calibrator I=10, Calibrator II=20, Calibrator III=40.

The ELISA values for each test specimen were determined using the formula in Example 1.

EXAMPLE 5

Test for Anti-β-2-Glycoprotein-1

Wells of microtiter polystryrene plate were coated with 3 μg of β2GP1 in 100 μl of 0.1 M carbonate buffer pH 9.6 and were kept overnight at 4° C. The plates were then washed with PBS and blocked with 2% BSA for 2 hours at room temperature. Plates were washed, dried, and used for detection of antibodies against β2GP1. The test specimen was added to the plate followed by incubation and washing. The procedure in Example 1 was followed to measure for β2GP1 antibodies.

The ELISA values for the calibrators used in this test system were as follows: Calibrator I=25, Calibrator II=75, and Calibrator III=150.

The ELISA values for each test specimen were determined using the formula in Example 1.

EXAMPLE 6

Test for Anti-Platelet Glycoproteins

Well of microtiter plate were coated with 3 μg of platelet glycoprotein in 100 μl of 0.1M carbonate buffer pH 9.6 and were kept overnight at 4° C. The plates were then washed with PBS and blocked with 2% BSA for 2 hours at room temperature. Plates were washed, dried, and used for detection of antibodies against platelet glycoproteins. The test specimen was added to the plate followed by incubation and washing. The procedure in Example 1 was followed to measure for platelet glycoprotein antibodies.

The ELISA values for the calibrators used in this test system were as follows: Calibrator I=10, Calibrator II=20, and Calibrator III=40.

The ELISA values for each test specimen were determined using the formula in Example 1.

EXAMPLE 7

Test for Immune Complexes

Wells of microtiter plates were coated with 3 μg of purified C1q in 100 μl of 0.1M carbonate buffer pH 9.6 and were kept overnight at 4° C. The plates were then washed with PBS and blocked with 2% BSA for 2 hours at room temperature. Plates were washed, dried, and used for detection of immune complexes. The test specimen was added to the plate followed by incubation and washing. The procedure in Example 1 was followed to measure for immune complexes.

The ELISA values for the calibrators used in this test system were as follows: Calibrator I=7, Calibrator II=15, and Calibrator III=30.

The ELISA values for each test specimen were determined using the formula in Example 1.

EXAMPLE 8

Analysis of Results

The results are analyzed as a panel. The values for myosin; oLDL; β2GP1; HSP60; and immune complexes were obtained from a set of healthy controls.

Thirty patients (15 men and 15 women) with known risk factors for cardiovascular disease were tested. These patients have a blood pressure greater than 140/80 and cholesterol/HDL level greater than 7.

The assays for antibodies were performed according to the preceding Examples. The results summarized in FIGS. 1-5 are expressed based on optical densities, which are easily converted to ELISA units.

Tables 2 and 3 and FIGS. 1-5 summarize the saliva IgA antibody levels against infectious agents as well as human tissue target antigens or epitopes in patients with possible cardiovascular disease and healthy control subjects.

TABLE 2

Saliva IgA Antibodies Against Specific and Non-Specific Autoantigens Involved in Cardiovascular Disease Expressed by O.D.'s From Patients With Possible Cardiovascular Disease

| SUBJECTS | MYOSIN | O-LDL | B-2-GP1 | HSP-60 | IMMUNE COMPLEX |
|---|---|---|---|---|---|
| 1 | 0.57 | 0.45 | 0.15 | 1.1 | 0.66 |
| 2 | 0.66 | 0.51 | 0.45 | 0.65 | 0.67 |
| 3 | 0.31 | 0.2 | 0.5 | 0.64 | 0.4 |
| 4 | 0.15 | 0.16 | 0.02 | 0.05 | 0.1 |
| 5 | 0.4 | 0.46 | 0.2 | 0.68 | 0.8 |
| 6 | 1.2 | 1.1 | 1.3 | 1.6 | 1.4 |
| 7 | 0.01 | 0.07 | 0.01 | 0.01 | 0.01 |
| 8 | 0.93 | 1.2 | 0.48 | 1.3 | 0.93 |
| 9 | 1.6 | 0.8 | 1.25 | 1.4 | 0.85 |
| 10 | 1.5 | 1.6 | 1.6 | 1 | 2 |
| 11 | 0.45 | 0.4 | 0.8 | 1.2 | 1.1 |
| 12 | 0.4 | 1.2 | 0.72 | 1.7 | 0.95 |
| 13 | 0.06 | 0.08 | 0.1 | 0.1 | 0.1 |
| 14 | 0.05 | 0.1 | 0.01 | 0.05 | 0.01 |
| 15 | 0.55 | 0.48 | 0.01 | 0.7 | 1.1 |
| 16 | 0.9 | 1.8 | 0.56 | 0.75 | 1.25 |
| 17 | 0.1 | 0.1 | 0.62 | 0.1 | 0.07 |
| 18 | 0.1 | 0.05 | 0.06 | 0.01 | 0.06 |
| 19 | 0.05 | 0.1 | 0.1 | 0.02 | 0.07 |
| 20 | 0.1 | 0.1 | 0.1 | 0.1 | 0.1 |
| 21 | 1.2 | 0.85 | 1.3 | 1.9 | 2.3 |
| 22 | 1.8 | 1.6 | 2.1 | 1.7 | 1.6 |
| 23 | 0.96 | 1.2 | 1.4 | 2.1 | 2.1 |
| 24 | 0.53 | 0.66 | 0.82 | 0.8 | 1.5 |
| 25 | 0.1 | 0.05 | 0.1 | 0.1 | 0.01 |
| 26 | 1.6 | 1.3 | 1.5 | 1.8 | 1.6 |
| 27 | 1.3 | 1.1 | 1.6 | 1.2 | 0.9 |
| 28 | 0.1 | 0.1 | 0.08 | 0.5 | 0.1 |
| 29 | 1.5 | 1.2 | 1.1 | 1.6 | 1.7 |
| 30 | 0.82 | 0.55 | 0.95 | 0.9 | 0.85 |
| Mean +/− S.D. | 0.52 +/− 0.55 | 0.65 +/− 0.54 | 0.67 +/− 0.60 | 0.85 +/− 0.67 | 0.85 +/− 0.69 |

TABLE 3

Saliva IgA Antibodies Against Specific and Non-Specific Autoantigens Involved in Cardiovascular Disease Expressed by O.D.'s From Healthy Controls

| SUBJECTS | MYOSIN | O-LDL | B-2-GP1 | HSP-60 | IMMUNE COMPLEX |
|---|---|---|---|---|---|
| 1 | 0.1 | 0.15 | 0.1 | 0.1 | 0.2 |
| 2 | 0.1 | 0.1 | 0.1 | 0.15 | 0.1 |
| 3 | 0.31 | 0.21 | 0.2 | 0.18 | 0.39 |
| 4 | 0.1 | 0.1 | 0.1 | 0.05 | 0.1 |
| 5 | 0.1 | 0.1 | 0.1 | 0.1 | 0.1 |
| 6 | 0.37 | 0.4 | 0.31 | 0.36 | 0.45 |
| 7 | 0.01 | 0.01 | 0.01 | 0.1 | 0.1 |
| 8 | 0.15 | 0.1 | 0.1 | 0.1 | 0.3 |
| 9 | 0.1 | 0.15 | 0.1 | 0.1 | 0.2 |
| 10 | 0.1 | 0.1 | 0.1 | 0.1 | 0.15 |
| 11 | 0.21 | 0.18 | 0.23 | 0.15 | 0.32 |
| 12 | 0.12 | 0.61 | 0.55 | 0.52 | 0.85 |
| 13 | 0.01 | 0.15 | 0.1 | 0.1 | 0.17 |
| 14 | 0.1 | 0.1 | 0.1 | 0.1 | 0.23 |
| 15 | 0.39 | 0.36 | 0.41 | 0.53 | 0.41 |
| 16 | 0.18 | 0.2 | 0.1 | 0.16 | 0.3 |
| 17 | 0.24 | 0.22 | 0.31 | 0.25 | 0.1 |
| 18 | 0.95 | 0.76 | 0.82 | 0.98 | 0.88 |
| 19 | 0.1 | 0.1 | 0.1 | 0.1 | 0.1 |
| 20 | 0.01 | 0.05 | 0.01 | 0.01 | 0.15 |
| 21 | 0.12 | 0.1 | 0.19 | 0.22 | 0.29 |
| 22 | 0.1 | 0.1 | 0.1 | 0.1 | 0.1 |
| 23 | 0.1 | 0.1 | 0.1 | 0.1 | 0.15 |
| 24 | 0.38 | 0.85 | 0.65 | 0.59 | 1.8 |
| 25 | 0.1 | 0.2 | 0.1 | 0.1 | 0.3 |

TABLE 3-continued

Saliva IgA Antibodies Against Specific and Non-Specific Autoantigens Involved
in Cardiovascular Disease Expressed by O.D.'s From Healthy Controls

| SUBJECTS | MYOSIN | O-LDL | B-2-GP1 | HSP-60 | IMMUNE COMPLEX |
|---|---|---|---|---|---|
| 26 | 0.1 | 0.1 | 0.1 | 0.15 | 0.1 |
| 27 | 0.15 | 0.26 | 0.31 | 0.39 | 0.35 |
| 28 | 0.1 | 0.1 | 0.1 | 0.1 | 0.26 |
| 29 | 0.45 | 0.38 | 0.3 | 0.51 | 0.43 |
| 30 | 0.1 | 0.1 | 0.1 | 0.1 | 0.15 |
| Mean +/- S.D. | 0.18 +/- 0.18 | 0.21 +/- 0.20 | 0.19 +/- 0.18 | 0.22 +/- 0.21 | 0.31 +/- 0.33 |

Figure 2:
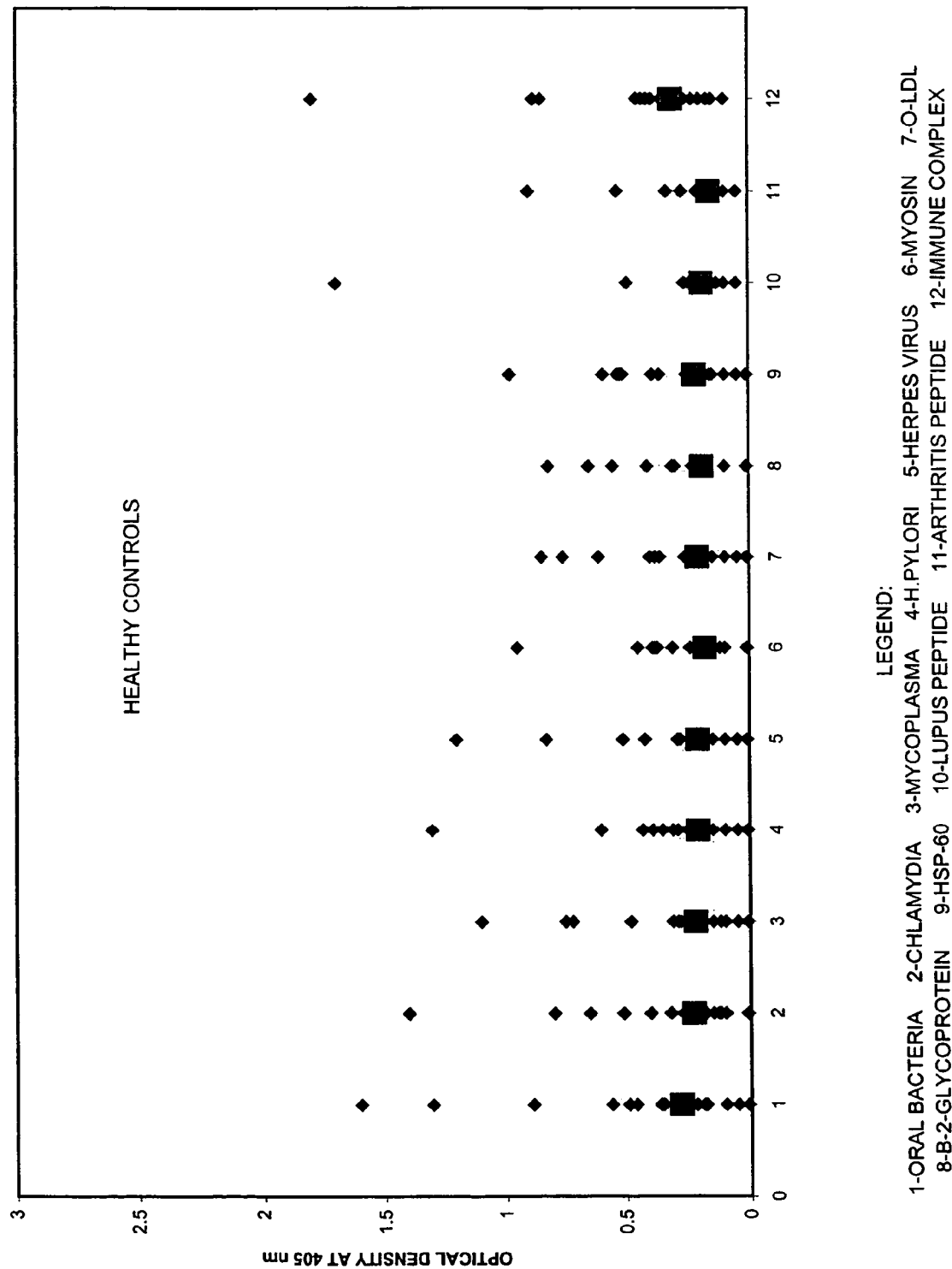
FIG. 2 is a graph showing saliva IgA antibodies against infectious agents, specific and non-specific autoantigens involved in cardiovascular disease and autoimmune disease expressed by O.D.'s from healthy controls.
Figure 3:
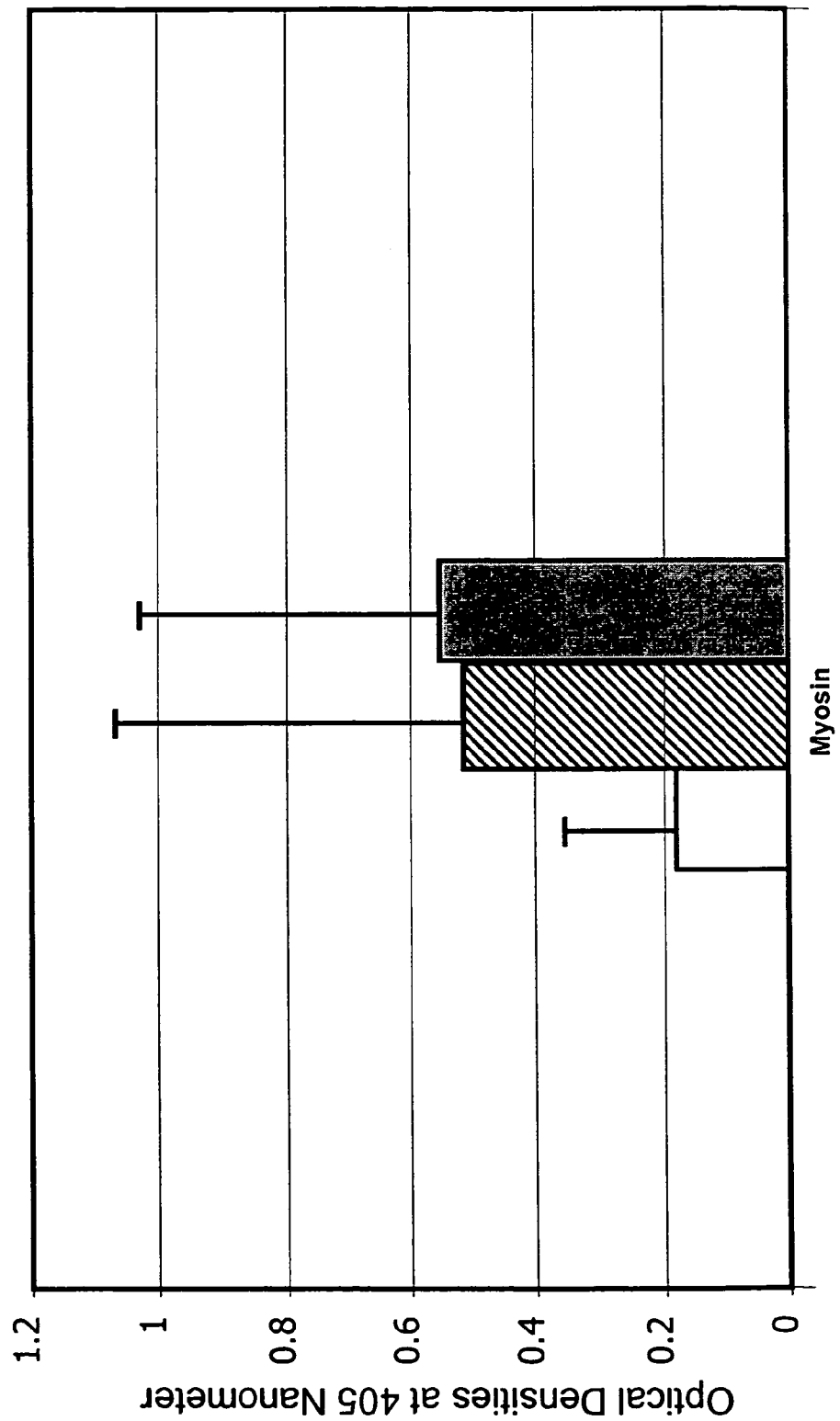
FIG. 3 is a graph showing the mean and standard deviation of thirty saliva samples of IgA antibody levels against myosin.
Figure 4:
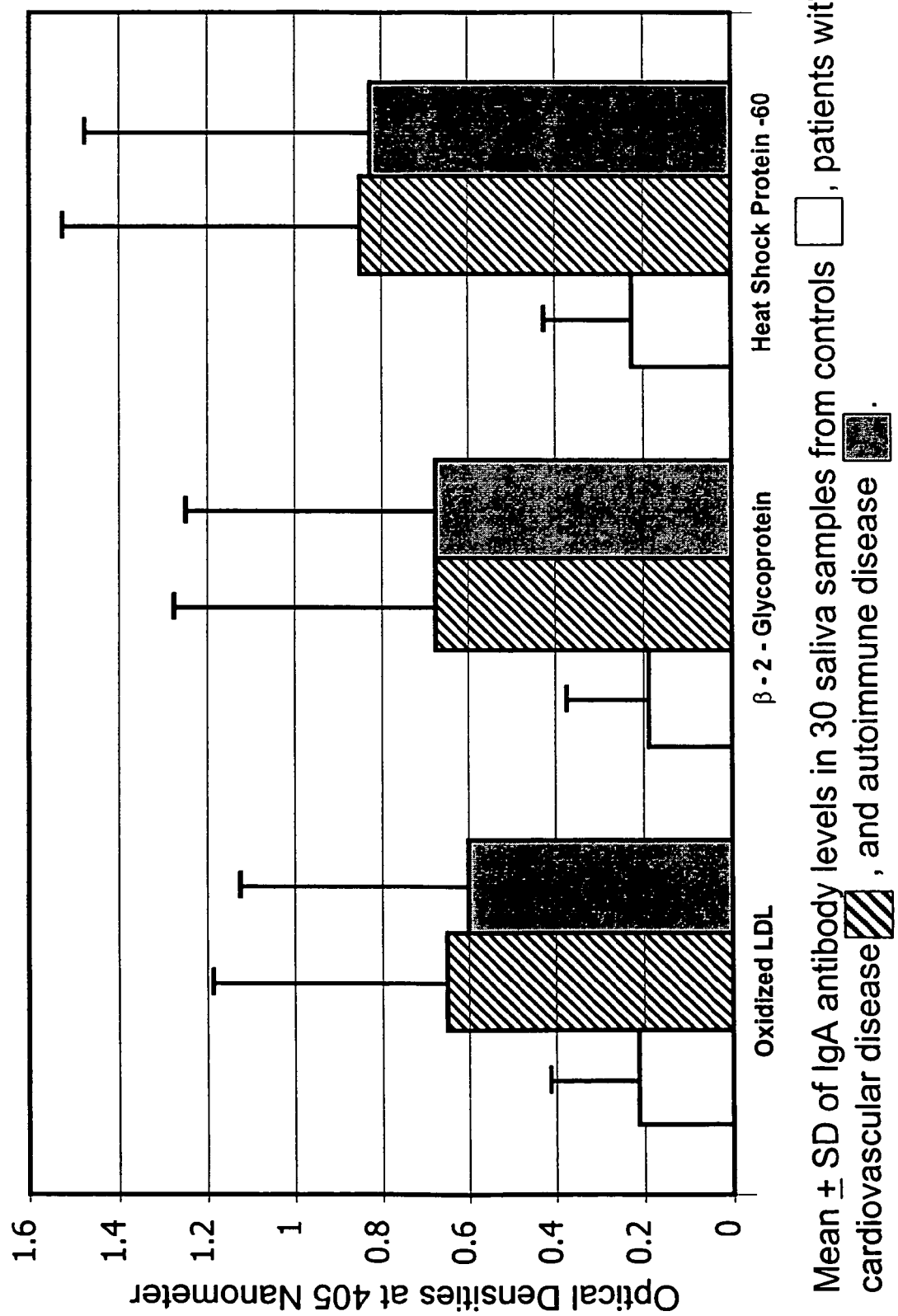
FIG. 4 is a graph showing the mean and standard deviation of thirty saliva samples of IgA antibody levels against oLDL, β-2-Glycoprotein, and HSP-60.
Figure 5:
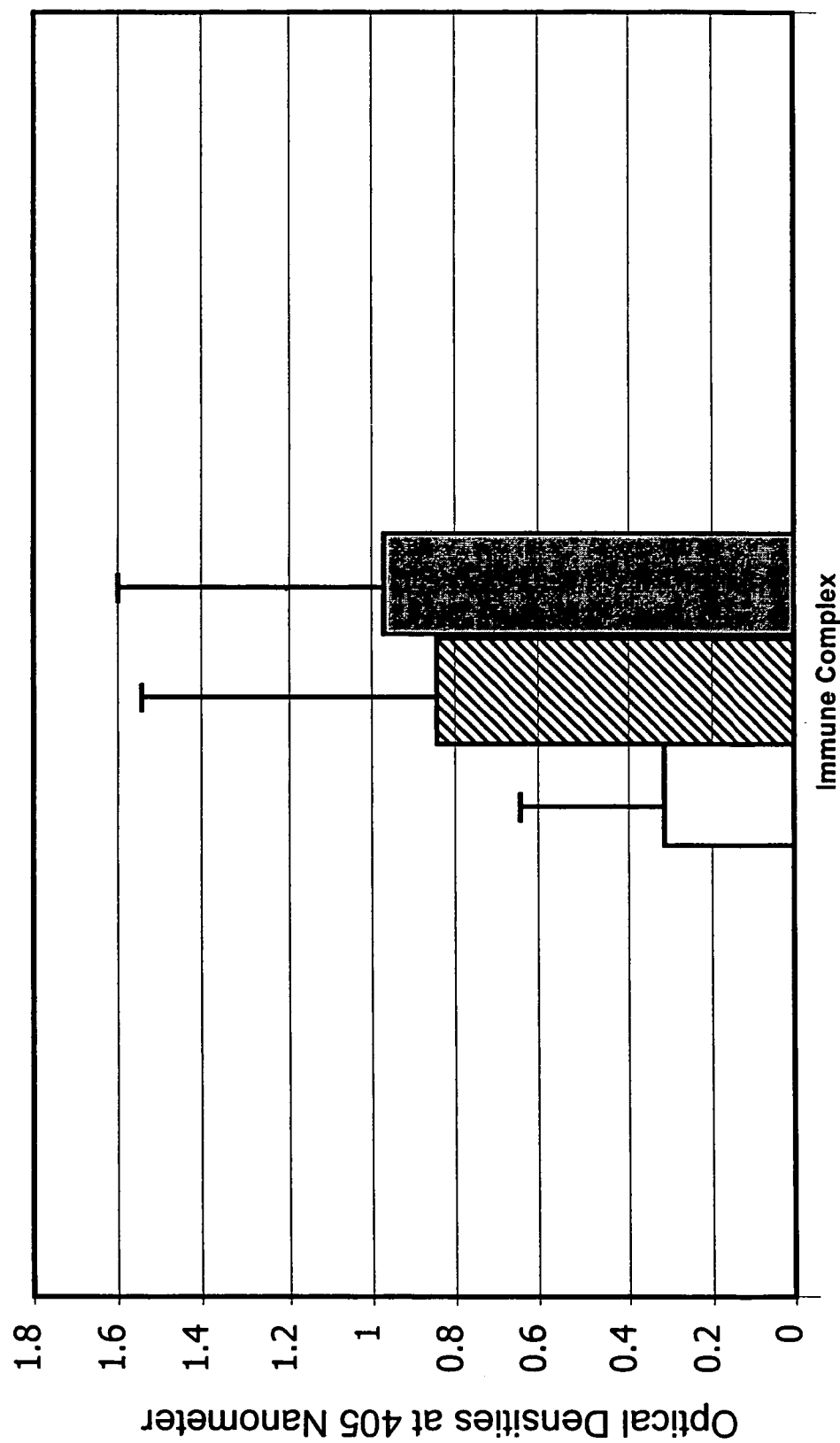
FIG. 5 is a graph showing the mean and standard deviation of thirty saliva samples of IgA antibody levels against immune complex.

FIGS. 1 and 2 illustrate each optical density as well as the mean of saliva IgA antibody level against 12 antigens. FIGS. 3-5 illustrate the mean and standard deviation of saliva IgA antibody levels from healthy controls and patients with cardiovascular disease.

Detection of IgA antibody in saliva against antigens of tissue antigens would help in early detection and prevention of cardiovascular disease. FIG. 6 shows data interpretation of antibody levels to infectious agents and human target tissue antigens relating to the possibility or presence of cardiovascular disease. The detection of above normal levels of saliva IgA antibody against the antigens listed in FIG. 6 can help to diagnose possible atherosclerosis. A normal level of antibody is defined as an average level of antibody taken from a set of healthy control individuals. For instance, the average levels are shown as the big squares on FIGS. 1 and 2.

The results of the test panels shown in combination with other clinical data and evaluation by the clinician allows for a faster and more accurate diagnosis of the above indications.

What is claimed is:

1. A method for determining the likelihood of cardiovascular disease in a patient suspected of having cardiovascular disease, comprising the steps of:

a) determining a level of a panel of antibodies in a saliva sample from said patient, wherein each antibody in said panel binds to a different autoantigen contained in a group of autoantigens or a corresponding recombinant antigen or synthetic peptide thereof, wherein the group of autoantigens comprises myosin, oxidized LDL, heat shock protein-60, β-2-glycoprotein-1, and C1q immune complexes; and b) comparing the level of antibodies determined in step a) with an average level of said antibodies in saliva from healthy control individuals, wherein
   at least about three fold higher than control levels of all five of said autoantigen antibodies indicate the likelihood of cardiovascular disease.

2. The method according to claim 1, wherein determining the level of antibodies in steps a) and b) is accomplished using an immunoassay.

3. The method according to claim 2, wherein the immunoassay is an ELISA.

4. The method according to claim 1, wherein the antibodies are IgA.

* * * * *